(12) United States Patent
Eckert et al.

(10) Patent No.: US 8,405,875 B2
(45) Date of Patent: Mar. 26, 2013

(54) VISIBLY-CODED MEDICATION LABEL AND ASSOCIATED METHOD, APPARATUS AND COMPUTER PROGRAM PRODUCT FOR PROVIDING SAME

(75) Inventors: Robert James Eckert, Eighty-Four, PA (US); Lloyd Lockerman, Pittsburgh, PA (US)

(73) Assignee: McKesson Automation Inc., Cranberry, PA (US)

( * ) Notice: Subject to any disclaimer, the term of this patent is extended or adjusted under 35 U.S.C. 154(b) by 835 days.

(21) Appl. No.: 12/409,210

(22) Filed: Mar. 23, 2009

(65) Prior Publication Data

US 2010/0241446 A1   Sep. 23, 2010

(51) Int. Cl.
*H04N 1/40* (2006.01)
(52) U.S. Cl. .......................................... 358/2.1; 358/296
(58) Field of Classification Search .................. 358/1.5, 358/1.9, 2.1, 296, 305, 400, 500, 468
See application file for complete search history.

(56) References Cited

U.S. PATENT DOCUMENTS

| | | | |
|---|---|---|---|
| 3,807,852 A * | 4/1974 | Hoydic | 346/135.1 |
| 4,717,042 A | 1/1988 | McLaughlin | |
| 4,785,969 A | 11/1988 | McLaughlin | |
| 4,847,764 A | 7/1989 | Halvorson | |
| 5,014,875 A | 5/1991 | McLaughlin et al. | |
| 5,190,185 A | 3/1993 | Blechl | |
| 5,314,243 A | 5/1994 | McDonald et al. | |
| 5,346,297 A | 9/1994 | Colson, Jr. et al. | |
| 5,377,864 A | 1/1995 | Blechl et al. | |
| 5,405,048 A | 4/1995 | Rogers et al. | |
| 5,431,299 A | 7/1995 | Brewer et al. | |
| 5,460,294 A | 10/1995 | Williams | |
| 5,468,110 A | 11/1995 | McDonald et al. | |
| 5,480,062 A | 1/1996 | Rogers et al. | |
| 5,520,450 A | 5/1996 | Colson, Jr. et al. | |
| 5,564,803 A | 10/1996 | McDonald et al. | |
| 5,593,267 A | 1/1997 | McDonald et al. | |
| 5,661,978 A | 9/1997 | Holmes et al. | |
| D384,578 S | 10/1997 | Wangu et al. | |
| 5,713,485 A | 2/1998 | Liff et al. | |
| 5,716,114 A | 2/1998 | Holmes et al. | |
| 5,745,366 A | 4/1998 | Higham et al. | |
| 5,761,877 A | 6/1998 | Quandt | |
| 5,797,515 A | 8/1998 | Liff et al. | |
| 5,805,456 A | 9/1998 | Higham et al. | |
| 5,842,976 A | 12/1998 | Williamson | |

(Continued)

OTHER PUBLICATIONS

U.S. Appl. No. 12/031,254, filed Feb. 14, 2008, Christie, et al.

*Primary Examiner* — Thomas D Lee
*Assistant Examiner* — Stephen M Brinich
(74) *Attorney, Agent, or Firm* — Alston & Bird LLP (57) ABSTRACT

A visibly-coded medication label and an associated method, apparatus and computer program product for providing a visibly-coded medication label are provided. A label having an attachment portion and an informational portion may be provided. The informational portion includes a plurality of regions having different visible indicia, such as different colors. Information may be imprinted upon the informational portion that is related to the medication with which the label is to be associated. At least one region that has visible indicia representative of the associated medication may be identified. At least one of the regions other than the region that has been identified to have visible indicia representative of the associated medication may then be overprinted and at least partially obscured. However, the region that has been identified to have visible indicia representative of the associated medication remains visible following the overprinting.

19 Claims, 3 Drawing Sheets

U.S. PATENT DOCUMENTS

| | | | |
|---|---|---|---|
| 5,878,885 A | 3/1999 | Wangu et al. |
| 5,880,443 A | 3/1999 | McDonald et al. |
| 5,883,806 A | 3/1999 | Meador et al. |
| 5,893,697 A | 4/1999 | Zini et al. |
| 5,905,653 A | 5/1999 | Higham et al. |
| 5,912,818 A | 6/1999 | McGrady et al. |
| 5,927,540 A | 7/1999 | Godlewski |
| 5,940,306 A | 8/1999 | Gardner et al. |
| 5,971,593 A | 10/1999 | McGrady |
| 6,003,006 A | 12/1999 | Colella et al. |
| 6,011,999 A | 1/2000 | Holmes |
| 6,021,392 A | 2/2000 | Lester et al. |
| 6,039,467 A | 3/2000 | Holmes |
| 6,065,819 A | 5/2000 | Holmes et al. |
| 6,068,156 A | 5/2000 | Liff et al. |
| 6,109,774 A | 8/2000 | Holmes et al. |
| 6,112,502 A | 9/2000 | Frederick et al. |
| 6,116,461 A | 9/2000 | Broadfield et al. |
| 6,151,536 A | 11/2000 | Arnold et al. |
| 6,170,230 B1 | 1/2001 | Chudy et al. |
| 6,176,392 B1 | 1/2001 | William et al. |
| 6,189,727 B1 | 2/2001 | Shoenfeld |
| 6,223,934 B1 | 5/2001 | Shoenfeld |
| 6,256,967 B1 | 7/2001 | Hebron et al. |
| 6,283,322 B1 | 9/2001 | Liff et al. |
| 6,289,656 B1 | 9/2001 | Wangu et al. |
| 6,338,007 B1 | 1/2002 | Broadfield et al. |
| 6,339,732 B1 | 1/2002 | Phoon et al. |
| 6,361,263 B1 | 3/2002 | Dewey et al. |
| 6,370,841 B1 | 4/2002 | Chudy et al. |
| 6,449,927 B2 | 9/2002 | Hebron et al. |
| 6,471,089 B2 | 10/2002 | Liff et al. |
| 6,497,342 B2 | 12/2002 | Zhang et al. |
| 6,499,270 B2 | 12/2002 | Peroni et al. |
| 6,532,399 B2 | 3/2003 | Mase |
| 6,564,121 B1 | 5/2003 | Wallace et al. |
| 6,581,798 B2 | 6/2003 | Liff et al. |
| 6,609,047 B1 | 8/2003 | Lipps |
| 6,610,379 B1 * | 8/2003 | Adams et al. ............ 428/40.1 |
| 6,611,733 B1 | 8/2003 | De La Huerga |
| 6,625,952 B1 | 9/2003 | Chudy et al. |
| 6,640,159 B2 | 10/2003 | Holmes et al. |
| 6,650,964 B2 | 11/2003 | Spano, Jr. et al. |
| 6,671,579 B2 | 12/2003 | Spano, Jr. et al. |
| 6,681,149 B2 | 1/2004 | William et al. |
| 6,742,671 B2 | 6/2004 | Hebron et al. |
| 6,755,931 B2 | 6/2004 | Vollm et al. |
| 6,760,643 B2 | 7/2004 | Lipps |
| 6,776,304 B2 | 8/2004 | Liff et al. |
| 6,785,589 B2 | 8/2004 | Eggenberger et al. |
| 6,790,198 B1 | 9/2004 | White et al. |
| 6,814,254 B2 | 11/2004 | Liff et al. |
| 6,814,255 B2 | 11/2004 | Liff et al. |
| 6,847,861 B2 | 1/2005 | Lunak et al. |
| 6,874,684 B1 | 4/2005 | Denenberg et al. |
| 6,892,780 B2 | 5/2005 | Vollm et al. |
| 6,895,304 B2 | 5/2005 | Spano, Jr. et al. |
| 6,975,922 B2 | 12/2005 | Duncan et al. |
| 6,985,797 B2 | 1/2006 | Spano, Jr. et al. |
| 6,996,455 B2 | 2/2006 | Eggenberger et al. |
| 7,010,389 B2 | 3/2006 | Lunak et al. |
| 7,014,063 B2 | 3/2006 | Shows et al. |
| 7,016,766 B2 | 3/2006 | William et al. |
| 7,040,504 B2 | 5/2006 | Broadfield et al. |
| 7,052,097 B2 | 5/2006 | Meek, Jr. et al. |
| 7,072,737 B2 | 7/2006 | Lunak et al. |
| 7,072,855 B1 | 7/2006 | Godlewski et al. |
| 7,077,286 B2 | 7/2006 | Shows et al. |
| 7,085,621 B2 | 8/2006 | Spano, Jr. et al. |
| 7,092,796 B2 | 8/2006 | Vanderveen |
| 7,093,755 B2 | 8/2006 | Jordan et al. |
| 7,100,792 B2 | 9/2006 | Hunter et al. |
| 7,103,419 B2 | 9/2006 | Engleson et al. |
| 7,111,780 B2 | 9/2006 | Broussard et al. |
| 7,139,639 B2 | 11/2006 | Broussard et al. |
| 7,150,724 B2 | 12/2006 | Morris et al. |
| 7,171,277 B2 | 1/2007 | Engleson et al. |
| 7,218,231 B2 | 5/2007 | Higham |
| 7,228,198 B2 | 6/2007 | Vollm et al. |
| 7,249,688 B2 | 7/2007 | Hunter et al. |
| 7,348,884 B2 | 3/2008 | Higham |
| 7,417,729 B2 | 8/2008 | Greenwald |
| 7,419,133 B2 | 9/2008 | Clarke et al. |
| 7,426,425 B2 | 9/2008 | Meek, Jr. et al. |
| 7,554,449 B2 | 6/2009 | Higham |
| 7,571,024 B2 | 8/2009 | Duncan et al. |
| 7,588,167 B2 | 9/2009 | Hunter et al. |
| 2005/0140135 A1 | 6/2005 | Miller et al. |

* cited by examiner

VISIBLY-CODED MEDICATION LABEL AND ASSOCIATED METHOD, APPARATUS AND COMPUTER PROGRAM PRODUCT FOR PROVIDING SAME

TECHNOLOGICAL FIELD

Embodiments of the present invention relate generally to medication labels and, more particularly, to visibly-coded medication labels and to associated methods, apparatus and computer program products for providing same.

BACKGROUND OF THE INVENTION

Medication may be stored or otherwise housed in a variety of packages. The packaging may include some pre-existing information printed on the package by the manufacturer. However, the packaging may lack the more specific labeling required by some purchasers or end users. For example, vials, syringes, and other packages used in the healthcare industry may include manufacturer information such as the name of the medication, the expiration date, etc., printed on the packaging, but may not include a bar code label required by a particular hospital in order to implement, for example, its point of care system. Additionally, the packaging of some medications may be changed over the course of time as medications are repackaged such that even though the original packaging may be appropriately labeled, the subsequent packaging may be lacking in terms of labeling. For example, the medication initially contained within an appropriately labeled vial may be drawn into a syringe. In instances in which the patient will not be administered the medication for some time with the medication, instead, remaining within the syringe, it may be desirable to label the otherwise unlabeled syringe.

Techniques have therefore been developed to permit labels to be printed containing the desired information including, in some instances, a bar code, for identifying the medication. These labels may be attached to the package containing the medication for future reference by a healthcare professional, a point of care system or the like prior to administration of the medication. In some instances, the labels include an adhesive portion that may be attached to the package and another non-adhesive portion that may extend outward from the package and may be imprinted with the information regarding the medication.

In addition to labeling packaging with alphanumeric information and/or a bar code identifying a medication, it may be desirable to also color-code the label in order to provide an additional, readily recognizable indication of the type of medication such that the healthcare personnel can have further assurance that the mediation to be administered to the patient is of the appropriate type. In this regard, different colors may be assigned to different types of drugs. Depending upon the type of medication in a package, the label to be attached to the package may be color coded so as to have the color that corresponds to the type of medication. This color coding may then serve as ready reference for a healthcare professional to insure that a package contains the appropriate type of medication prior to its administration to a patient.

A label may be appropriately color coded by using an ink jet printer, laser printer or other color printer to imprint a colored region upon the label with the color corresponding to the type of medication in the package to which the label will be attached. However, an ink jet printer, laser printer or other color printer capable of reliably printing an appropriately colored region upon a label may be more expensive than is desirable and, in any event, would sometimes disadvantageously require additional capital expenditures since label printing has typically been done with black-and-white printers. Furthermore, an error may occur in color printing if one of the primary color reservoirs runs empty or clogs; thus green may appear as blue if the yellow ink is empty. Additionally, in instances in which a medication is repackaged, it may be desirable to print a label for the new package at the site of the repackaging. For example, a medication cart, such as an anesthesia cart, that is moved throughout a healthcare facility may desirably include a printer for printing various documents including, for example, labels for various medication packages including, for example, those medications that are repackaged while on the cart. However, because of their desired mobility, medication carts are generally relatively small such that the space available on a medication cart is limited. Although a medication cart may include a computer with a black-and-white printer, it could be prohibitive from both a cost and a space standpoint to include an ink jet printer, laser printer or other color printer for the purpose of color coding medication labels printed on the medication cart.

As an alternative to printing the color codes on the labels, stickers having the various colors assigned to the different types of medication may be used to color code the medication labels. In this regard, a sticker having a color corresponding to the appropriate type of medication may be affixed to the label. With respect to a medication cart, the use of stickers to color code medication labels requires that additional supplies, that is, the stickers of the various colors, be carried aboard the medication cart. Additionally, the use of stickers to color code medication labels also requires that an additional manual step be taken in order to select and apply the appropriately colored sticker to the label.

As such, it would be desirable to provide an improved technique for appropriately color coding a medication label. In this regard, it would be desirable to provide a technique for color coding a medication label that is cost effective and that does not meaningfully increase the burden upon the healthcare professionals. Additionally, in instances in which the medication labeling is to be performed onboard a medication cart, it would be also desirable to support color-coded labeling in a manner which does not require the dedication of additional space onboard the medication cart, such as to store supplies, support an additional color printer or the like.

BRIEF SUMMARY OF THE INVENTION

A visibly-coded medication label and an associated method, apparatus and computer program product for providing a visibly-coded medication label are provided according to embodiments of the present invention. As described below, embodiments of the present invention permit medication labels to be visibly coded, such as by color coding, in a manner that is both efficient and does not appreciably, if at all, increase the burden upon a healthcare professional. Further, embodiments of the present invention may be implemented onboard a medication cart in such a manner that little, if any, additional space onboard the medication cart is required in order to store supplies, support an ink jet printer, laser printer or other color printer or the like.

In one embodiment, the method of providing a visibly-coded medication label is provided in which a label having an attachment portion and an informational portion is initially provided. The attachment portion may include an at least partially translucent substrate with an adhesive backing. The informational portion includes a plurality of regions having different visible indicia such that at least one region has a different visible appearance than another region. The method of this embodiment also prints information upon the informational portion related to the medication with which the label is to be associated. For example, the printed information may include alphanumeric characters and/or a bar code identifying the medication.

The method of this embodiment also identifies at least one of the regions that has visible indicia representative of the associated medication. The method then overprints at least one of the regions other than the at least one region that has been identified to have visible indicia representative of the associated medication. As such, the at least one region that has been identified to have visible indicia representative of the associated medication remains visible following the overprinting. By overprinting, the visible indicia of the at least one overprinted region is at least partially obscured and, in one embodiment, is completely obscured. While any number of regions may be identified to have visible indicia representative of the associated medication and, as a result, remain visible following the overprinting, the method of one embodiment overprints all regions except for a single region identified to have visible indicia representative of the associated medication.

In one embodiment, the informational portion includes a plurality of differently colored regions. As such, at least one of the regions that has a color representative of the associated medication may be identified with the region(s) other than the at least one region that has been identified to have the color representative of the associated medication being overprinted. As such, the at least one region that has been identified to have the color representative of the associated medication remains visible even though the color of the overprinted region(s) has been at least partially, if not completely, obscured.

By providing a label having a plurality of regions with different visible indicia, such as different colors, and then overprinting the regions that have visible indicia unrelated to the medication, the resulting label will be visibly coded, such as by being color coded, in a manner that corresponds with the medication with which the label is to be associated. However, by overprinting regions that initially include various visible indicia as opposed to printing the visible indicia, the method of this embodiment does not require an ink jet printer, a laser printer or other color printer and can, instead, be implemented with a black-and-white printer, such as the thermal transfer printer already carried by a number of medication carts. Additionally, the method of this embodiment does not require a healthcare professional to manually perform a number of additional steps in order to appropriately visibly code a medication label. As such, the method of embodiments of the present invention can be practiced in both a cost effective and efficient manner.

An apparatus and computer program product are also provided according to other embodiments of the present invention for providing a visibly-coded medication label. In this regard, the apparatus may include a processor configured to cause information to be printed upon the informational portion of a label with the information being related to the medication with which the label will be associated. The processor may also identify at least one of the regions that has visible indicia representative of the associated medication and then cause at least one of the regions other than the region that has been identified to have visible indicia representative of the associated medication to be overprinted. As such, the at least one region that has been identified to have visible indicia representative of the associated medication will remain visible while the visible indicia of the at least one region that has been overprinted will be at least partially obscured, thereby providing a medication label that has been appropriately visible coded for the medication with which the label is to be associated. In another embodiment, the computer program product may include at least one computer-readable storage medium having computer-executable program instructions stored therein. The computer-executable program instructions may include program instructions configured to cause information to be printed upon the informational portion related to the medication with which the label is to be associated. The computer-executable program instructions may also include program instructions configured to identify at least one of the regions that has visible indicia representative of the associated medication and program instructions configured to cause at least one of the regions other than the at least one region that has been identified to have visible indicia representative of the associated medication to be overprinted. As such, the at least one region that has been identified to have visible indicia representative of the associated medication remains visible, while the visible indicia of the at least one region has been overprinted is at least partially obscured, thereby again providing a medication label that has been appropriately visibly coded.

A color-codable medication label may also be provided in accordance with one embodiment of the present invention. In this regard, the color-codable medication label may include an attachment portion configured to be attached to a medication. In one embodiment, the attachment portion includes an at least partially translucent substrate with an adhesive backing. The color-codable medication label of this embodiment also includes an informational portion connected to the attachment portion. The informational portion may include a first area configured to be printed with information related to the medication and a second area having a plurality of differently colored regions such that at least one region has at different color than another region. At least one of the regions has a color representative of the medication.

In another embodiment, a visibly-coded medication label is provided that includes an attachment portion configured to be attached to a medication. In one embodiment, the attachment portion may include an at least partially translucent substrate with an adhesive backing. The visibly-coded medication label of this embodiment also includes an informational portion connected to the attachment portion. The informational portion includes a first area having information related to the medication and a second area having a plurality of regions having different visible indicia such that at least one region has a different visible appearance than another region. The second area also includes a mask at least partially obscuring and, in one embodiment, completely obscuring the visible indicia of at least one of the regions. However, the mask fails to cover all of the regions such that at least one of the regions having visible indicia representative of the medication remains visible. In one embodiment, for example, the mask at least partially obscures all regions except for a single region identified to have visible indicia representative of the associated medication.

In one embodiment of the visibly-coded medication label, the second area of the informational portion includes a plurality of differently colored regions. In this embodiment, the mask at least partially obscures at least one of the regions other than the at least one region that has been identified to have the color representative of the associated medication. As such, the at least one region that has been identified to have the color representative of the associated medication remains visible while the color of the at least one masked region is at least partially obscured.

BRIEF DESCRIPTION OF THE SEVERAL VIEWS OF THE DRAWING(S)

Having thus described the invention in general terms, reference will now be made to the accompanying drawings, which are not necessarily drawn to scale, and wherein:

DETAILED DESCRIPTION OF THE INVENTION

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements. Like numbers refer to like elements throughout.

Figure 1:
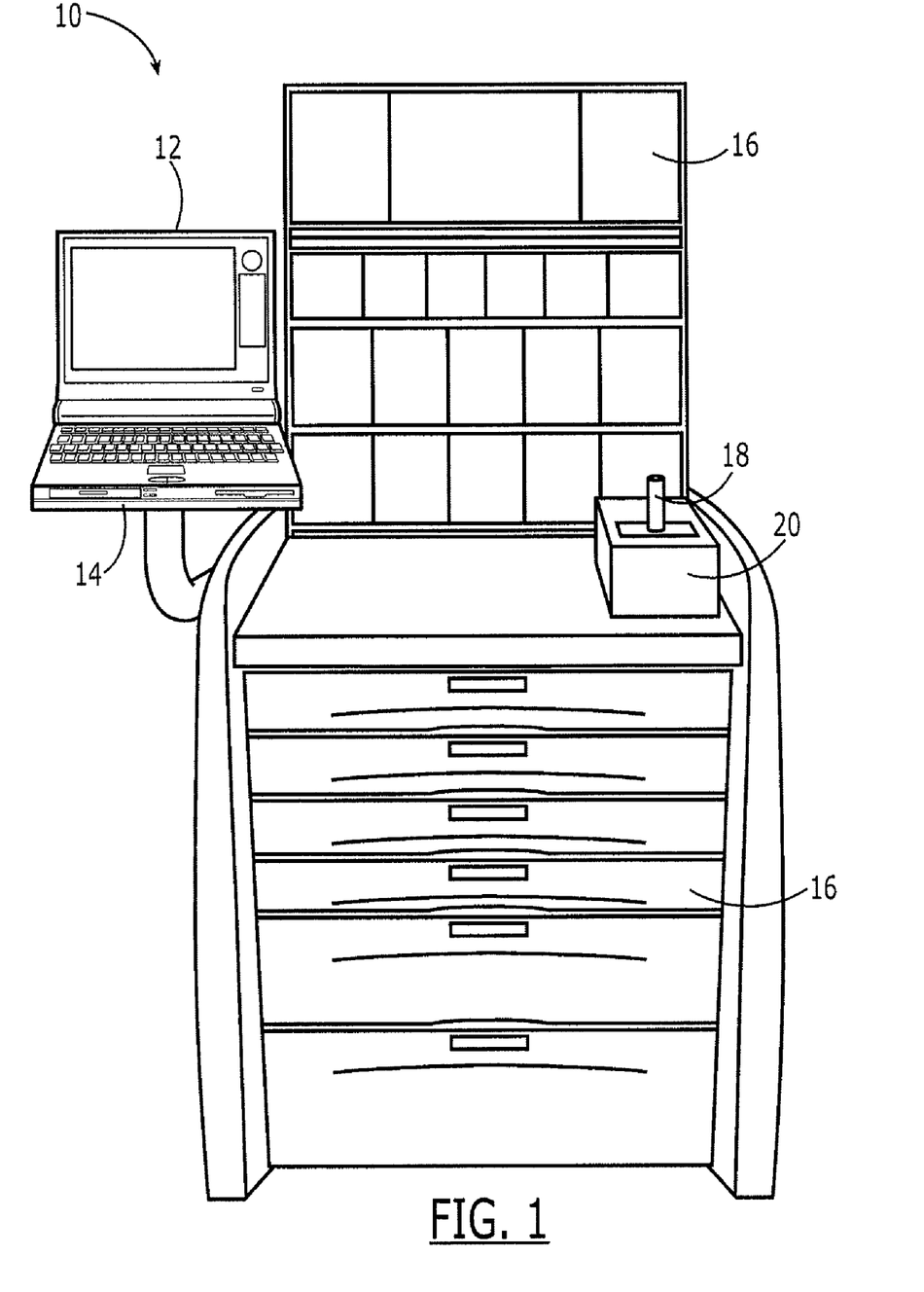
FIG. 1 is a schematic view of a medication cart according to one embodiment of the present invention.

A method, apparatus and computer program product for providing a visibly-coded medication label are described herein in conjunction with various embodiments of the present invention. As illustrated in FIG. 1, the method, apparatus and computer program product of embodiments of the present invention may be implemented by or upon a medication cart, such as an anesthesia cart. However, embodiments of the method, apparatus and computer program product may be differently implemented by or upon platforms or in environments other than upon a medication cart such that the medication cart described hereinafter is provided by way of example, but not of limitation.

Referring now to FIG. 1, a medication cart 10 is illustrated. In this regard, a medication cart provides a platform for doctors, anesthesiologists, nurses, pharmacists and other healthcare personnel to store, transport and dispense medications to their patients. A medication cart may come in a variety of forms including a mobile medication dispensing cart, a medication cabinet, a nurse server, etc. For example, an anesthesiologist may have his or her own medication cart, which stores various medications as well as items or devices used for dispensing and delivering those medications, e.g. syringes, gloves, etc. during a given work day. As shown in FIG. 1, a medication cart may include a computer system, which is discussed in more detail below with regard to FIG. 5, which may be used to print labels that will be associated with medications dispensed from the medication cart. Additionally, the computer system may be used to access information associated with the medication and the dispensing/delivery devices stored by the medication cart, as well as information associated with the patients for whom medications may be dispensed from the medication cart at a given point in time. In one embodiment, some or all of this information may be stored locally in memory associated with the computer system. In one embodiment, information associated with the medications and the dispensing/delivery devices stored in the medication cart and their location within the medication cart, may be input to the computer system at or near the time at which the medication cart is first put into use and automatically updated thereafter as medications are added and/or dispensed.

Alternatively, or in addition, some or all of the information may be accessed by the computer system from a remote location, for example, via wireless communication network, on a central server or system associated with the healthcare facility in which the medication cart is being used.

Using the computer system, a healthcare worker may request information regarding a patient, as well as input information regarding the medications he or she is dispensing. Accordingly, the computer system may include a display screen 12, a keyboard 14 and/or other input and/or output devices which are not shown and which may include, for example, a speaker, bar code reader, a radio frequency identification (RFID) tag reader, and the like.

The medication cart 10 may also include one or more drawers 16 for storing the various medications and dispensing/delivery devices. The drawers may be arranged in various configurations, but, in one embodiment, one or more of the drawers further include one or more pockets for holding medications and/or dispensing/delivery devices.

As described hereinafter, a technique for providing visibly-coded medication labels is provided. As such, the medication cart 10 of the illustrated embodiment may also include one or more medication labels 18, e.g. stock labels, that may be processed in a manner described herein in order to be appropriately visibly coded. Additionally, the medication cart may include a printer 20 for printing information upon the medication label and for appropriately visibly coding the medication label. Although various printers may be employed, embodiments of the method, apparatus and computer program product of the present invention may utilize a conventional black-and-white printer, such as a conventional black-and-white thermal transfer printer, that operates under control of the computer system and is already carried by many medication carts, thereby conserving space abroad the medication cart.

Figure 2:
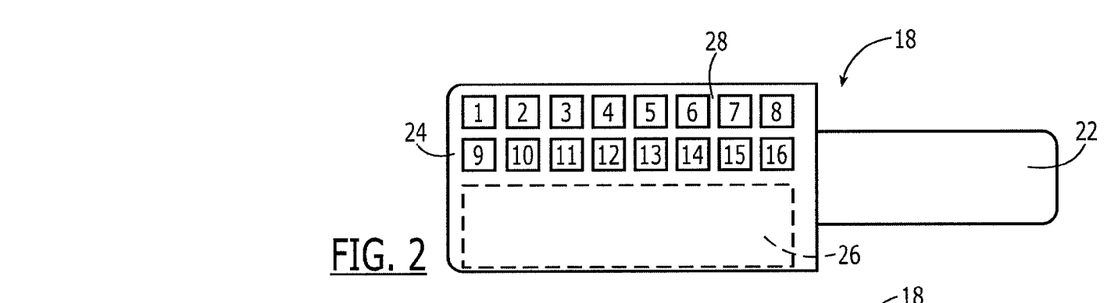
FIG. 2 is an illustration of a visibly-codable medication label according to one embodiment to the present invention.

The medication labels 18 that are processed in accordance with embodiments of the present invention may include an attachment portion 22 and an informational portion 24 as shown, for example, in FIG. 2. The attachment portion may be configured to be attached to a medication. In this regard, an attachment portion is considered to be configured to be attached to a medication in instances in which the attachment portion is to be actually affixed to the medication itself as well as in instances in which the attachment portion is to be affixed to a package, e.g., vial, syringe, etc., that contains the medication. The attachment portion may include an at least partially translucent substrate having an adhesive backing to facilitate subsequent affixation to the medication. In one embodiment, the attachment portion is transparent, while in other embodiments, the attachment portion only partially translucent. By not being opaque and, instead, being at least partially translucent, healthcare personnel may still be able to view any information on that portion of the package to which the attachment portion of the medication label is affixed through the at least partially translucent attachment portion. Thus, the affixation of the medication label to the medication need not obscure a portion of the package which may include information, for example, regarding the medication or its administration that a healthcare worker may desire to review.

The informational portion 24 is connected to the attachment portion 22. In the illustrated embodiment, the informational portion includes a first area 26 configured to be printed with information related to the medication to which the medication label 18 will be attached and a second area 28 having a plurality of regions (designated 1-16 in the embodiment of FIG. 2) having different visible indicia. In this regard, at least one region has a different visible appearance than another region, and, in one embodiment, each region has a different visible appearance than every other region. While the medication label may be configured to include a variety of different types of visible indicia, such as different cross-hatching schemes, different textures or the like, the medication label of one embodiment includes an informational portion having a plurality of differently colored regions with at least one region having a different color than another region and, in one embodiment, with each region having a different color than every other region.

Regardless of the type of visible indicia that is employed by a medication label 18, the visible indicia may be selected such that each different visible indicia is representative of a different category or type of medication. With respect to a medication label having an informational portion 24 with differently colored regions, each different color may be associated with and representative of a different category or type of medication. In the embodiment of FIG. 2, for example, the regions designated 1-16 may be associated with and representative of 16 different categories or types of medications. While the different visible indicia, such as the different colors, may be associated with a variety of different categories or types of medication in any number of manners, one exemplary color scheme for a medication label configured to individually identify twelve different categories of medications is as follow:

| Drug Category | Pantone Color |
| --- | --- |
| Induction agents | Yellow |
| Tranquilizers | Orange 151 |
| Muscle relaxants | Florescent red 805 |
| Relaxant antagonists | Florescent red 805/White diagonal stripes |
| Narcotics | Blue 297 |
| Narcotic antagonists | Blue 297/White diagonal stripes |
| Major tranquilizers | Salmon 156 |
| Narcotic/tranquilizer | Combinations Blue 297/Salmon 156 |
| Vasopressors | Violet 256 |
| Hypertensive agents | Violet 256/White diagonal stripes |
| Local anesthetics | Grey 401 |
| Anticholinergic agents | Green 367 |

As illustrated by the foregoing listing, the different colors that are associated with the different categories or types of medications need not necessarily be different solid colors, but may, instead, include combinations of colors and stripes or other color features with all of the various combinations being considered different colors.

Figure 3:
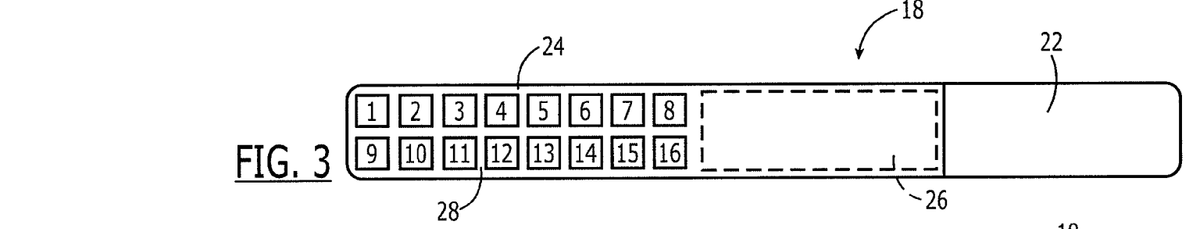
FIG. 3 is an illustration of a visibly-codable medication label according to another embodiment of the present invention.

Although one example of a medication label 18 is depicted in FIG. 2 in accordance with one embodiment of the present invention, medication labels of other embodiments may be differently configured. In this regard, another example of a medication label is depicted in FIG. 3. As shown in conjunction with the medication label of FIG. 2, the medication label of FIG. 3 also includes an attachment portion 22 and an informational portion 24 including first and second areas with the first area 26 configured to be imprinted with information regarding the medication to which the label is to be affixed and the second area 28 including a plurality of regions (again designated 1-16) that have different visible indicia associated with different types of medication. In contrast to the medication label of FIG. 2, however, the medication label of FIG. 3 is configured somewhat different with the first and second areas of the informational portion extending in a linear or serial fashion such that the medication label has a consistent width along its length. In contrast, the medication label of FIG. 2 includes an informational portion having the first and second areas positioned in parallel alongside one another such that the width of the informational portion is greater than the width of the attachment portion, although the length of the medication label of FIG. 2 may be correspondingly less than that of the medication label of FIG. 3. While two embodiments of a medication label are depicted in FIGS. 2 and 3, medication labels according to embodiments of the present invention may include a number of other configurations without departing from the spirit and scope of the present invention. Additionally, the relative sizes of the attachment portion and the informational portion as well as the relative sizes of the first and second areas of the informational portion may be varied without departing from the spirit and scope of the present invention.

Figure 4:
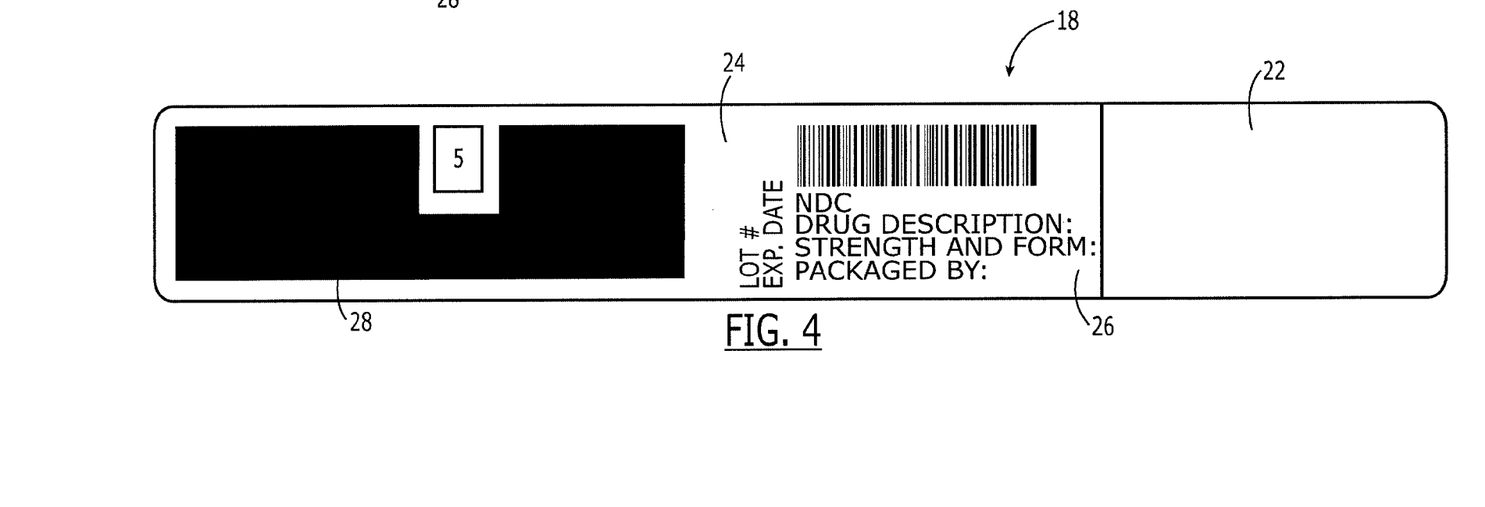
FIG. 4 is an illustration of a visibly-coded medication label according to one embodiment of the present invention once information has been imprinted upon the informational portion and a plurality of the visibly-coded regions have been overprinted.

According to embodiments of the present invention, a medication label 18, such as the medication labels of the embodiments of FIGS. 2 and 3, may be printed in order to appropriately identify the medication with which the label is to be associated, such as by being affixed thereto. As shown in FIG. 4, for example, the label may be printed such that information is imprinted upon the informational portion 24 and, more particularly, upon the first area 26 of the informational portion. The information imprinted upon the first area may have a variety of different types and formats, but in the illustrated embodiment may include alphanumeric characters and a code, such as a bar code, that provide information regarding the medication with which the medication label is to be associated. In this regard, the alphanumeric characters may form a human readable section which may include a National Drug Code (NDC) field, a generic name field, a strength field, a drug name field, an expiration date field, a drug form field, a packaged-by field, a lot number field and/or other fields as desired in order to appropriately identify the medication with which the label is to be associated. Additionally, the first area of the informational portion may include a machine readable section including, for example, a European Article Number/Universal Product Code (EAN/UPC) compliant bar code or the like.

In addition to printing information within the first area 26 of the informational portion 24, one or more of the regions having different visible indicia within the second area 28 may be overprinted. However, at least one of the regions remains visible with the visible indicia of the region that remains visible being representative of the medication with which the label 18 is to be associated. As among the various regions having different visible indicia, the particular region that has visible indicia representative of the medication with which the label is to be associated may be identified and the other regions having visible indicia that are not representative of the medication with which the label is to be associated may then be overprinted such that only the region having the visible indicia representative of the medication with which the label is to be associated remains visible. In order to overprint one or more of the regions, printing is performed upon the label so as to overlie the regions having visible indicia that are not representative of the medication to which the label is to be affixed. As such, the overprinting of these regions at least partially obscures the underlying visible indicia of the regions that are not representative of the medication with which the label is to be associated. As such, the overprinting effectively serves to create a mask at least partially obscuring the underlying visible indicia of the overprinted regions. The regions need only be partially obscured in order to visibly differentiate the overprinted regions from the one or more regions having visible indicia representative of the medication to which the label is to be affixed and which are not overprinted. However, the regions that are not representative of the medication with which the label will be affixed may be overprinted in such a manner as to completely visibly obscure the underlying visible indicia of those regions in other embodiments. By completely obscuring the underlying visible indicia of the regions that are not representative of the medication with which the label is to be associated, the resulting medication label may even more clearly delineate and highlight the region that is not overprinted and, therefore, not masked as a result of its visible indicia being representative of the medication with which the label is to be affixed or otherwise associated.

By way of example and with reference to the above listing of medication categories and associated pantone colors, it may be determined that the medication with which a label 18 is to be associated is a narcotic. As such, the stock medication label may be printed to appropriately identify the specific narcotic with a combination of both alphanumeric characters and a bar code in the first area 26 of the informational portion 24. Additionally, the plurality of differently colored regions may be overprinted such that only the single region having the Blue 297 color representative of a narcotic is free of the overprinting and remains visible (as indicated by the region designated 5 in FIG. 4). Once the medication label has been affixed to the medication, such as by adhering the attachment portion 22 to the medication, healthcare personnel can quickly recognize the medication as a narcotic by noting the Blue 297 color of the medication label and can then obtain more detailed information regarding the particular narcotic by means of the information printed within the first area of the informational portion and readable by either a human and/or a machine. Thus, the healthcare personnel can quickly confirm that the appropriate type of medication is on hand prior to the administration.

Figure 5:
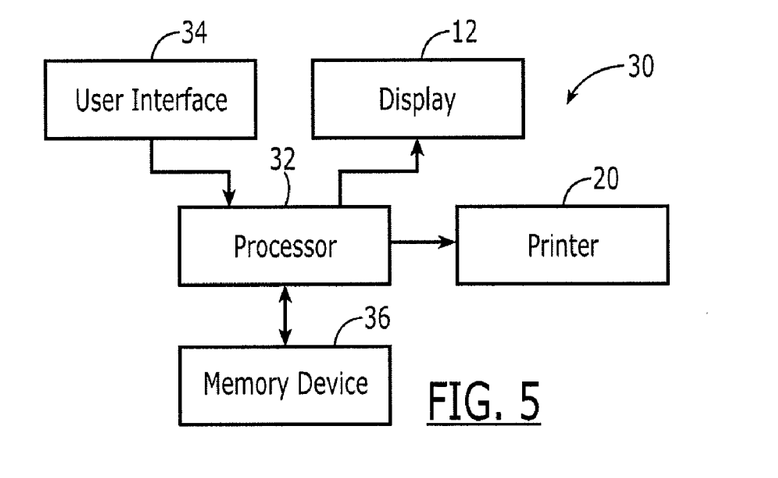
FIG. 5 is a block diagram of a computing system in accordance with one embodiment of the present invention.

As described above, the provision of a visibly-coded medication label 18 may be implemented by means of a computer system, such as that carried by a medication cart 10 as generally shown in FIG. 1. While the computer system may be embodied in a variety of different manners without departing from the spirit and scope of the present invention, the computer system 30 of one embodiment is depicted in FIG. 5. The computer system may be implemented in various fashions including a dedicated processor, a personal computer, a workstation or any other type of appropriately configured processor. For purposes of example, however, the computer system of one embodiment is depicted in FIG. 5 and may be mounted upon a medication cart as shown in FIG. 1. The computer system may include a processor 32, a user interface 34, a display 12, a memory device 36 and a printer 20. The memory device may be configured to store information, data, applications, instructions or the like for enabling the computing device to carry out various functions in accordance with exemplary embodiments of the present invention. For example, the memory device may be configured to store information associated with the medication and the dispensing/delivery devices carried by the medication cart, as well as information associated with the patients for whom medications may be dispensed from the medication cart at a given point in time. Additionally or alternatively, the memory device may be configured to store instructions for execution by the processor.

The processor 32 may be embodied in a number of different ways. For example, the processor may be embodied as a processing element, a coprocessor, a controller or various other processing means or devices including integrated circuits such as, for example, an ASIC (application specific integrated circuit) or FPGA (field-programmable gate array) or combinations thereof. In an exemplary embodiment, the processor may be specifically configured to execute instructions stored in the memory device 36 or otherwise accessible to the processor. As such, whether configured by hardware or software methods, or by a combination thereof, the processor may represent an entity capable of performing operations according to embodiments of the present invention while configured accordingly. Thus, for example, when the processor is embodied as an ASIC, FPGA or the like, the processor may be specifically configured hardware for conducting the operations described herein. Alternatively, as another example, when the processor is embodied as an executor of software instructions, the instructions specifically configure the processor to perform the algorithms and operations described herein.

The user interface 34 may be in communication with the processor 32 to receive an indication of a user input at the user interface and/or to provide an audible, visual, mechanical or other output to the user. As such, the user interface may include, for example, a keyboard 14, a mouse, a joystick, a trackball, a microphone, a speaker, or other input/output mechanisms. As noted above, the computer system 30 may also include a display 12 to present information to a user and, in some embodiments, to serve as a graphical user interface via which user input is provided to the computer system, such that the display may also comprise at least a portion of the user interface by serving as in input device, e.g., a touchscreen.

As noted above, the computer system 30 also includes a printer 20 for printing labels 18 in accordance with embodiments of the present invention. In this regard, the printer may be in communication with the processor 32 such that the processor can direct the printing operations including the information imprinted upon the labels.

Figure 6:
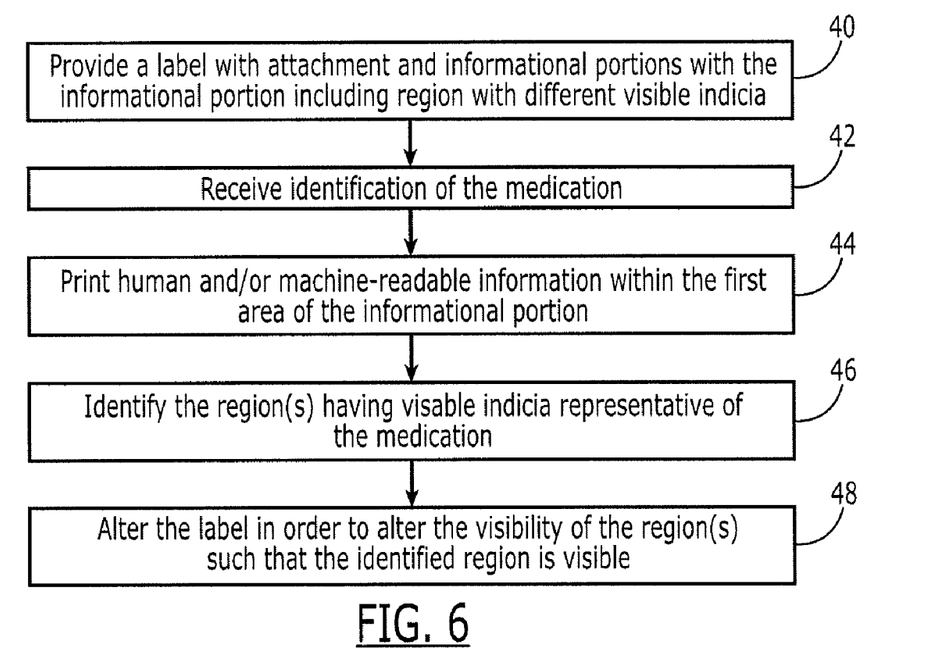
FIG. 6 is a flow chart of the operations to be performed in accordance with one embodiment of the present invention.

As shown in FIG. 6, in operation, one or more labels 18, each having an attachment portion 22 and an informational portion 24 having a plurality of regions with different visible indicia, such as different colors, may be provided and loaded into the printer 20. See operation 40 of FIG. 6. The processor 32 may then receive an indication of the medication as shown in operation 42 of FIG. 6, such as by either user entry via the user interface 34 or via the scanning of a bar code or other machine readable code carried by a vial or other medication package from which the medication is to be dispensed. Based upon the identification of the medication, the processor can then determine the information to be imprinted upon the first area 26 of the informational portion 24 and can also determine the category of the medication from among the plurality of categories that have different visible indicia, such as different colors, associated therewith. In one embodiment, the memory device 36 stores information regarding a plurality of different types of medication including, for each medication, information to be imprinted upon the first area of the informational portion as well as the category of the medication. As such, in response to the identification of the medication, the processor can retrieve the necessary information from the memory device in order to properly imprint and otherwise process the medication label including the information to be imprinted and the category of the medication.

Once the processor 32 has obtained the information regarding the medication, the processor may direct the printer 20 to imprint the information, such as the alphanumeric characters and/or the bar code, upon the first area 26 of the informational portion 24 of the label 18. See operation 44 of FIG. 6. Additionally, the processor may direct or otherwise cause the printer to overprint all of the regions having visible indicia that is not representative of the medication to which the label is to be affixed such that only the one or more regions having visible indicia representative of the medication to which the label is to be affixed remain free of the overprinting so as to remain visible. See operation 48 of FIG. 6. In this regard, the processor and/or the printer may be configured with information defining the layout of the medication label including the relative positions and sizes of the attachment portion 22 and the first and the second areas of the informational portion as well as the size and position of each different regions within the second area 28 of the informational portion such that the processor and/or the printer is configured to identify the location upon the label of the region(s) that are to be overprinted and the region(s) that are to remain free of the overprinting. See operation 46 of FIG. 6. Following the overprinting, the resulting medication label including the mask that at least partially obscures the visible indicia of the regions that do not correspond to the medication to which the label is to be affixed may be removed from the printer and affixed to the medication for use in subsequent identification of the medicine.

As described above, by utilizing label stock 18 that already includes a plurality of regions having the different visible indicia that will be utilized to distinguish the different categories of medication, the visible indicia need not be printed upon the medication label in the field, such as upon a medication cart 10. Instead, the regions having the visible indicia that are not representative of the respective medication may simply be overprinted and masked. As such, this overprinting can be performed by a conventional black-and-white printer 20, such as a black-and-white thermal transfer printer that may otherwise be carried by a medication cart, so as to provide for visible coding the medication labels in a cost effective manner in the field without consuming additional space upon a medication cart or the like. Additionally, the medication labels may be readily visibly coded without healthcare personnel having to perform any appreciable amount of additional effort.

Many modifications and other embodiments of the inventions set forth herein will come to mind to one skilled in the art to which these inventions pertain having the benefit of the teachings presented in the foregoing descriptions and the associated drawings. For example while the overprinting has been described above to overprint all regions except for a single region having a color representative of the medication to which the label 18 will be affixed, the overprinting may be performed so as to leave two or more regions exposed if the two or more regions each have visible indicia representative of the medication to which the label will be affixed. In this manner, an even greater number of categories of medications may be uniquely identified by the same number of regions by relying upon different combinations of the visible indicia. By way of another example, the overprinting has been illustrated in FIG. 4 to include a solid, contiguous block that overlies a plurality of regions. However, in another embodiment, the individual regions may be separately overprinted with some blank space remaining between the separately overprinted regions. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

That which is claimed:

1. A method of providing a visibly-coded medication label, the method comprising:
    providing a label having an attachment portion and an informational portion, wherein the informational portion comprises a plurality of regions having different visible indicia such that at least one region has a different visible appearance than another region and such that the visible indicia of the plurality of regions are concurrently visible without obscuration;
    printing information upon the informational portion related to a medication with which the label is to be associated, wherein the information is printed upon an area of the informational portion that is distinct from the plurality of regions;
    identifying at least one of the regions that has visible indicia representative of the associated medication; and
    overprinting at least one of the regions other than the at least one region that has been identified to have visible indicia representative of the associated medication such that the at least one region that has been identified to have visible indicia representative of the associated medication remains visible, wherein overprinting the at least one region comprises at least partially obscuring the visible indicia of the at least one overprinted region.

2. A method according to claim 1 wherein providing the label comprises providing the label having the informational portion comprising a plurality of differently colored regions, wherein identifying at least one of the regions comprises identifying at least one of the regions that has a color representative of the associated medication, and wherein overprinting comprises overprinting at least one of the regions other than the at least one region that has been identified to have the color representative of the associated medication such that the at least one region that has been identified to have the color representative of the associated medication remains visible while at least partially obscuring the color of the at least one overprinted region.

3. A method according to claim 1 wherein overprinting further comprises completely obscuring the visible indicia of the at least one overprinted region.

4. A method according to claim 1 wherein overprinting further comprises overprinting all regions except for a single region identified to have visible indicia representative of the associated medication.

5. A method according to claim 1 wherein printing information comprises printing at least one of alphanumeric characters or a barcode.

6. A method according to claim 1 wherein providing the label comprises providing the label having the attachment portion comprising an at least partially translucent substrate with an adhesive backing.

7. An apparatus for providing a visibly-coded medication label having an attachment portion and an informational portion, wherein the informational portion comprises a plurality of regions having different visible indicia such that at least one region has a different visible appearance than another region and such that the visible indicia of the plurality of regions are concurrently visible without obscuration, the apparatus comprising a processor configured to:

cause information to be printed upon the informational portion related to a medication with which the label is to be associated, wherein the information is printed upon an area of the informational portion that is distinct from the plurality of regions;

identify at least one of the regions that has visible indicia representative of the associated medication; and cause at least one of the regions other than the at least one region that has been identified to have visible indicia representative of the associated medication to be overprinted such that the at least one region that has been identified to have visible indicia representative of the associated medication remains visible while the visible indicia of the at least one region that has been overprinted is at least partially obscured.

8. An apparatus according to claim 7 wherein the informational portion of the label comprises a plurality of differently colored regions, wherein the processor is configured to identify at least one of the regions by identifying at least one of the regions that has a color representative of the associated medication, and wherein the processor is configured to cause at least one of the regions to be overprinted by causing at least one of the regions other than the at least one region that has been identified to have the color representative of the associated medication to be overprinted such that the at least one region that has been identified to have the color representative of the associated medication remains visible while the color of the at least one overprinted region is at least partially obscured.

9. An apparatus according to claim 7 wherein the processor is configured to cause at least one of the regions to be overprinted by causing the visible indicia of the at least one overprinted region to be completely obscured.

10. An apparatus according to claim 7 wherein the processor is configured to cause at least one of the regions to be overprinted by causing all regions except for a single region identified to have visible indicia representative of the associated medication to be overprinted.

11. A computer program product for providing a visibly-coded medication label having an attachment portion and an informational portion, wherein the informational portion comprises a plurality of regions having different visible indicia such that at least one region has a different visible appearance than another region and such that the visible indicia of the plurality of regions are concurrently visible without obscuration, wherein the computer program product comprises at least one non-transitory computer-readable storage medium having computer-executable program instructions stored therein, the computer-executable program instructions comprising:

program instructions configured to cause information to be printed upon the informational portion related to a medication with which the label is to be associated, wherein the information is printed upon an area of the informational portion that is distinct from the plurality of regions;

program instructions configured to identify at least one of the regions that has visible indicia representative of the associated medication; and program instructions configured to cause at least one of the regions other than the at least one region that has been identified to have visible indicia representative of the associated medication to be overprinted such that the at least one region that has been identified to have visible indicia representative of the associated medication remains visible while the visible indicia of the at least one region that has been overprinted is at least partially obscured.

12. A computer program product according to claim 11 wherein the informational portion of the label comprises a plurality of differently colored regions, wherein the program instructions configured to identify at least one of the regions are further configured to identify at least one of the regions that has a color representative of the associated medication, and wherein the program instructions configured to cause at least one of the regions to be overprinted are further configured to cause at least one of the regions other than the at least one region that has been identified to have the color representative of the associated medication to be overprinted such that the at least one region that has been identified to have the color representative of the associated medication remains visible while the color of the at least one overprinted region is at least partially obscured.

13. A computer program product according to claim 11 wherein the program instructions configured to cause at least one of the regions to be overprinted are further configured to cause the visible indicia of the at least one overprinted region to be completely obscured.

14. A computer program product according to claim 11 wherein the program instructions configured to cause at least one of the regions to be overprinted are further configured to cause all regions except for a single region identified to have visible indicia representative of the associated medication to be overprinted.

15. A visibly-coded medication label comprising:
an attachment portion configured to be attached to a medication; and
an informational portion connected to the attachment portion, the informational portion comprising a first area having information related to the medication and a second area having a plurality of regions having different visible indicia such that at least one region has a different visible appearance than another region, wherein the first area is spaced apart from the second area such that the information of the first area is distinct from the plurality of regions of the second area, and wherein the second area further comprises a mask at least partially obscuring the visible indicia of at least one of the regions, wherein the mask fails to cover all of the regions such that at least one of the regions having visible indicia representative of the medication remains visible.

16. A visibly-coded medication label according to claim 15 wherein the second area of the informational portion comprises a plurality of differently colored regions, and wherein the mask at least partially obscures at least one of the regions other than the at least one region that has been identified to have the color representative of the associated medication such that the at least one region that has been identified to have the color representative of the associated medication remains visible while the color of the at least one masked region is at least partially obscured.

17. A visibly-coded medication label according to claim 15 wherein the mask completely obscures the visible indicia of the at least one masked region.

18. A visibly-coded medication label according to claim 15 wherein the mask at least partially obscures all regions except for a single region identified to have visible indicia representative of the associated medication.

19. A visibly-coded medication label according to claim 15 wherein the attachment portion comprises an at least partially translucent substrate with an adhesive backing.

\* \* \* \* \*